United States Patent [19]

Grasel et al.

[11] Patent Number: 5,296,518
[45] Date of Patent: Mar. 22, 1994

[54] HYDROPHILIC POLYURETHANEUREA FOAMS CONTAINING NO TOXIC LEACHABLE ADDITIVES AND METHOD TO PRODUCE SUCH FOAMS

[75] Inventors: Timothy G. Grasel, Calabasas, Calif.; Clifford A. Ferrin, Baltimore, Md.; James L. Guthrie, Ashton, Md.; Clifton L. Kehr, Silver Spring, Md.

[73] Assignee: Hampshire Chemical Corp., Lexington, Mass.

[21] Appl. No.: 809,363

[22] Filed: Dec. 18, 1991

Related U.S. Application Data

[63] Continuation-in-part of Ser. No. 705,276, May 24, 1991, and a continuation-in-part of Ser. No. 764,589, Sep. 24, 1991.

[51] Int. Cl.$^5$ ............................................. C08G 18/00
[52] U.S. Cl. .................................. 521/176; 521/159; 521/162; 521/163; 424/84
[58] Field of Search ............... 521/176, 159, 162, 163; 424/84

[56] References Cited

U.S. PATENT DOCUMENTS

| | | |
|---|---|---|
| 3,812,619 | 5/1974 | Wood et al. . |
| 3,890,254 | 6/1975 | Guthrie . |
| 3,903,232 | 9/1975 | Wood et al. . |
| 3,969,498 | 7/1976 | Catania et al. ...................... 424/445 |
| 4,132,839 | 1/1979 | Marans et al. ...................... 521/159 |
| 4,137,200 | 1/1979 | Wood et al. . |
| 4,160,076 | 7/1979 | Guthrie et al. . |
| 4,731,247 | 3/1988 | Wolford et al. ...................... 426/1 |
| 5,065,752 | 11/1991 | Sessions et al. .................. 428/317.1 |

FOREIGN PATENT DOCUMENTS

| | | |
|---|---|---|
| 0295055 | 12/1988 | European Pat. Off. . |
| 0446156 | 9/1991 | European Pat. Off. . |

*Primary Examiner*—John Kight, III
*Assistant Examiner*—D. V. C. Truong
*Attorney, Agent, or Firm*—Nields & Lemack

[57] ABSTRACT

Hydrophilic polyurethane urea foams which are made without toxic, leachable additives are disclosed. High molecular weight, isocyanate-terminated, ethylene oxide-rich prepolymers are used in place of surfactants to make the foams.

24 Claims, No Drawings

HYDROPHILIC POLYURETHANEUREA FOAMS CONTAINING NO TOXIC LEACHABLE ADDITIVES AND METHOD TO PRODUCE SUCH FOAMS

This application is a continuation-in-part of our co-pending applications U.S. Ser. No. 705,276 filed May 24, 1991, and U.S. Ser. No. 764,589, filed Sep. 24, 1991, which are incorporated herein by reference in their entirety.

BACKGROUND OF THE INVENTION

This invention relates to water-absorbing polyurethaneurea foams that contain no toxic leachable additives, and yet have the desirable physical properties commonly conferred by surfactants or other additives. The inventors have found that fine-celled, even-textured and reasonably hydrophilic foams can be prepared by incorporating high molecular weight, isocyanate-terminated prepolymers. These prepolymers function in the present invention to stabilize the cell structure of the foam, and to confer a hydrophilic character. Normally, a surfactant is added to confer such properties. The high molecular weight prepolymers are not known to be surfactants.

These foams are especially useful to make medical implants or wound care products because they are potentially safer for the patient.

Polyurethane foams are materials which can be used in diverse items such as coatings, absorbent pads and electronic component packaging. Naturally, the different applications can require different physical properties. In the medical field, for example, it is highly desirable to maximize the safety of any material which can come into contact with a patient's tissues and bodily fluids. In this case, the focus is on an effort to produce a foam which has the highly desirable fine-celled texture and hydrophilic nature of known foams, but which contains no potentially toxic or irritating additives.

Although the known foams appear to function very well in medical applications, the body is known to be a very aggressive environment. Thus the possibility exists that any nonbound additive contained in the foam might be leached out. In some circumstances this can be a useful feature, as in the metered dosing of a medicament over a period of time. However, it is preferable that this feature is controlled, and that the presence of potentially irritating components be minimized.

It is generally accepted in the polyurethane foam art that surface-active materials are essential ingredients in the manufacture of polyurethane foams (Woods, G., *The ICI Polyurethanes Book*, London: imperial Chemical Industries and John Wiley & Sons, Ltd., 1978, p. 48 ISBN 0471 914266. They help to control the size of the foam cells by stabilizing the gas bubbles formed during nucleation. In flexible foam manufacture, surfactants also help to control the degree of cell opening and increase the operating margin between the extremes of foam collapse, when cell opening occurs before the reaction mixture has sufficiently polymerized beyond its "gel point".

The production of hydrophilic polyurethane foams without surfactant is known and is described in the literature. However, it is known to all those who work with polyurethaneurea polymers that foams made without surfactants have many coarse cells, have little uniformity in cell size, and have very hydrophobic character. Furthermore, the inventors have found that known non-cytotoxic surfactants generally result in reticulated cell structures and medium to very coarse cell sizes. It is very desirable to make fine-celled, hydrophilic foams without surfactants or by using approved non-cytotoxic surfactants while having very fine cells and achieving very soft foams. This has not been achieved in hydrophilic foams made using either the one-shot or prepolymer routes.

The use of surface-active agents in polyurethane-urea foams is taught to be critical to the attainment of many useful properties (See U.S. Pat. No. 4,160,076, issued Jul. 3, 1979 to Guthrie). U.S. Pat. No. 3,890,254, issued Jun. 17, 1975 to Guthrie also teaches the use of particular surfactants, in conjunction with particular blowing agents, to make fully reticulated foams.

For hydrophilic foams made using an excess of (reactive) water, the presence of surfactants, even if hydroxy-functional, generally does not affect the progress of the reaction. Water competes with the hydroxyl groups in the isocyanate reaction, and there is no assurance that the hydroxyl groups on the surfactant will react at all. Because they do not take part in the chemical reaction, these surfactants are not bound into the structure of the foam. For that reason, the surfactants might be easily leached out of the foam under the right conditions. The inventors have found that certain isocyanate-capped high molecular weight molecules can be used instead of the non-bound surfactants to produce hydrophilic polyurethaneurea foams with uniform open or reticulated cell structure.

These isocyanate-capped species react into the foam and cannot be leachable when the foam is used. This finding was especially unexpected, because it was generally felt that reactive molecules would not be sufficiently mobile to orient at the polymer-air interface and have a cell-stabilizing action.

It was not expected that a high molecular weight, isocyanate-terminated, ethylene oxide-rich prepolymer would show cell-stabilizing action, because by itself it is not known to be a surfactant.

It was not expected that small amounts of these isocyanate-terminated polyols could modify the action of existing surfactants and allow the use of nocytotoxic surfactants to produce fine-celled, hydrophilic foams. The known non-cytotoxic surfactants are generally used to make coarse, reticulated cell structures in polyurethaneurea foams.

It is therefore an object of this invention to produce water-absorbing polyurethaneurea foams, from prepolymers, that contain no toxic surfactants or related leachable additives. These foams may be especially desirable for skin-contacting applications, such as cosmetic pads or wound care products, where freedom from toxic or irritating additives would be advantageous. Also, foamed materials for medical or implant applications benefit from having no toxic additives.

Other objects and advantages of this invention will be illuminated by the disclosure herein.

SUMMARY OF THE INVENTION

An isocyanate-terminated prepolymer is made from a high molecular weight (>2000) polyalcohol, preferably a diol or triol. This prepolymer is mixed with the conventional prepolymer used to make a hydrophilic foam as taught in U.S. Pat. No. 4,137,200. Cell size control and polymer wettability are significantly improved over the case where the prepolymer is not incorporated.

Additionally, when this prepolymer is present, surfactants that would not normally result in fine-celled, wettable foams can be used to make a fine-celled, wettable foam.

Furthermore, such foams, when formulated with a non-toxic foaming agent and a non-cytotoxic surfactant, can be made with reduced amounts of water even when compared to those foams disclosed by Wood in U.S. Pat. No. 4,137,200. As used herein, "hydrophilic" foams are those which accept and absorb water rapidly, either when a water drop is placed on a flat foam surface or when a foam is immersed in a pool of water. "Hydrophilic" foams will absorb the water drop in a reasonable amount time, and will vertically wick and absorb water from the pool.

DETAILED DESCRIPTION OF THE PREFERRED EMBODIMENTS

One embodiment of the invention uses foams prepared from a prepolymer described by U.S. Pat. No. 4,137,200 issued to Wood et al Jan. 30, 1979, the contents of which are incorporated herein by reference. The prepolymers described in the Wood patent are the reaction products of mixtures comprising (a) a first polyol having a hydroxyl functionality of at least 2 and a number average molecular weight range of 200 to 20,000 and which contains at least 40 mole percent oxyethylene, (b) a second polyol having a hydroxyl functionality in the range of about 3 to 8 and (c) a polyisocyanate having an average isocyanate functionality in the range of about 2.0 to 2.8.

The hydroxyl groups of the first and second polyols are capped by reaction with the polyisocyanate. This reaction may be carried out in an inert moisture-free atmosphere such as a nitrogen blanket, at atmospheric pressure at a temperature in the range of from about 0° C. to about 120° C. for a period of time of up to about 20 hours depending upon the temperature, presence of catalysts, and degree of agitation. This reaction may be effected also under atmospheric conditions provided the reaction mixture is not exposed to excess moisture.

The first polyol is preferably a hydrophilic oxyalkylene polyol containing at least about 40%, and more preferably about 80 to 100%, oxyethylene. The balance should be oxypropylene, oxybutylene, etc. Suitable examples include random ethylene/propylene oxide oligomers which have a number average molecular weight in the range of about 1000-2500 and are hydrophilic, water soluble and liquid at room temperature.

The second polyol provides crosslinking ability and is preferably a generally linear polyol having at least 3, and preferably between 3 and 8 hydroxyl groups. Usually monomeric polyols having 3 to 4 hydroxyl groups per mole are employed. A suitable example of the second polyol is trimethylolpropane.

A suitable polyisocyanate mentioned in the '200 patent to Wood is toluene diisocyante. Other polyisocyanates which may be used include the following:

PAPI(A polyaryl polymethylenepolyisocyanate as defined in U.S. Pat. No. 2,683,730)
triphenylmethane-4,4',4,"-triisocyanate,
benzene-1,3,5-triisocyanate,
toluene-2,4,6-triisocyanate,
diphenyl-2,4,4'-triisocyanate,
xylene diisocyanate,
chlorophenylene diisocyanate,
diphenylmethane-4,4'- diisocyanate,
naphthalene-1,5-diisocyanate,
xylene-alpha,3,3'-dimethyl-4,4'-biphenylene diisocyanate
3,3'-dimethoxy-4,4'-biphenylene diisocyanate,
2,2',5,5'-tetramethyl-4,4'-biphenylene diisocyanate,
4,4'-methylenebis(phenylisocyanate),
4,4'-sulfonylbis(phenylisocyanate),
4,4'-methylene di-orthotolylisocyanate,
ethylene diisocyanate,
hexamethylene diisocyanate
methylene bis(cyclohexyl isocyanate),
trimethylenediisocyanate,
isophorone diisocyanate, and
2,2,4- trimethyl-1,6-hexane diisocyanate.

Mixtures of any one or more of the above-mentioned organic isocyanates may be used as desired. Further, suitable mixtures can include combinations of dimers and trimers derived from diisocyanates such as those described above. Especially suitable isocyanates are those which are readily commercially available and have a high degree of isocyanate reactivity.

Prepolymers made from toluene diisocyanate are commercially available as HYPOL® polymers FHP 2000, 2002 and 3000 from W. R. Grace & Co.-Conn. These prepolymers are made from varying ratios of the first and second polyols with enough toluene diisocyanate to cap all of the hydroxyl groups.

To prepare the prepolymers described in the Wood patent, the polyols and polyisocyanate can be reacted by two methods described therein. Briefly, the first method involves first reacting a molar excess of polyisocyanates with the first and second polyols. The isocyanate-containing polyols are then blended in various molar proportions so that the resulting product mixture has an average isocyanate functionality greater than two. Upon reacting the blend of the two isocyanate containing polyols with water, as described below, a crosslinked foam results.

The second method of preparing the prepolymer involves a post-addition step of isocyanate. Briefly, the first and second polyols are reacted in less than molar excess isocyanate and then later used to make foams by adding isocyanates and water. This method and the method in the above paragraph are described more fully in the '200 patent to Wood, the contents of which have been incorporated herein by reference.

Further, during either of the above two prepolymer forming reactions, it has been helpful to measure the isocyanate level by titration periodically during the reaction. From these periodic measurements, one can determine the point at which all the hydroxyl groups of the polyol (and crosslinking agent) will have reacted with an isocyanate. Thus, if the first method is being used and the end point by titration has not been reached, additional reaction time will be required. However, if the reaction is carried out too far, side reactions of the isocyanate groups may occur, causing the viscosity of the resulting prepolymer to increase to the point where it may become difficult to mix the prepolymer with water.

Another useful embodiment can use foams made from oxyethylene-containing, multifunctional polyols, e.g. triols, tetrols etc. Oxyethylene-containing triols can be prepared by polymerizing ethylene oxide in the presence of a polyfunctional hydroxyl-containing starter component, such as glycerol, trimethylolpropane or trimethylolethane. The molecular weight of these polymeric triols may be varied greatly, depending on the number of moles of ethylene oxide used in the reaction with the starter component. Starter components such as pentaerythritol and sucrose likewise treated with ethylene oxide lead to polymeric polyoxyethylene tetrols and hexols, respectively. Suitable examples of other oxyethylene-containing, multifunctional polyols, e.g. tetrols, which can be used to make these foams are found in the examples of U.S. Pat. Nos. 3,903,232 issued Sep. 2, 1975 and 3,812,619 issued May 28, 1974 to Wood et al, the contents of which are incorporated herein by reference.

When using multifunctional polyols the prepolymers are prepared by reacting the hydroxyl groups of the triol with a polyisocyanate similar to the methods demonstrated in the '232 patent. See Examples 1–4 and 7 of the '232 patent.

To effect foaming of the prepolymer, the prepolymer is simply combined with particular aqueous components. These methods are well known in the art as the '200 patent to Wood indicates. Briefly, it is known that water (aqueous reactant) can be added in weight ratios of prepolymer:water in the range of about 0.05:1 to about 10:1. More preferable weight ratios are about 1:1 to about 4:1. For instance, when the prepolymer is capped with methylene bis(cyclohexyl isocyanate), foams suitable for this invention can be produced from a prepolymer:water weight ratio in the range of about 2:1 to 6:1. This results in a foam having a density ranging from about 0.02 g/cc to 0.05 g/cc.

Surfactants are generally added to the aqueous reactant to adjust the texture and appearance of the foam, i.e. such as the cell size, shape, etc., as well as to prevent the formation of splits in the resulting foam buns. In particular, buns made without surfactants tend to be coarse in cell size and have large distributions in cell sizes.

The prepolymers which act as a surfactant in this system are isocyanate-capped triols and higher polyols which are made up of at least 75% oxyethylene monomers. Methods of making such prepolymers are described in copending U.S. Ser. Nos. 510,260 and 682,502, which are incorporated herein by reference in their entirety. The polyols have molecular weights of about 7000 to about 30,000, with essentially all of the hydroxyl groups capped with polyisocyanate. The prepolymers are prepared by reacting the selected triols and higher polyols with polyisocyanate at an isocyanate-to-hydroxyl ratio of about 1.8 to about 2.2 so that essentially all of the hydroxyl groups of the polyols are capped with polyisocyanate. As specific examples of this class of prepolymers, prepolymers from the BIOPOLO ® polyurethane prepolymers series and the HYPOLO ® hydrogel series available from Grace Specialty Chemicals Co., W. R. Grace & Co.-Conn., will be particularly suitable.

High molecular weight ethylene oxide-based triols and higher polyols are preferably used to prepare the prepolymers and hydrated polymers of the present invention. The polyol molecular weight prior to capping with polyisocyanate should be about 7000 to about 30,000 NW. It is preferred to use trihydroxy compounds (triols) in the preparation of the polyols which are the precursors to the prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

The prepolymers of this invention are formed by reacting the hydroxyl groups of the triols or higher polyols described above with polyisocyanates. "Polyisocyanate" as used herein is intended to refer to both diisocyanates and polyisocyanates, as appropriate, except as indicated by specifying the use of difunctional or polyfunctional isocyanates. Isocyanate end-capped (i.e., isocyanate-terminated) prepolymers are formed. The choice of the polyisocyanate will depend on such factors as biocompatibility of the end product and differential NCO reactivities.

Aliphatic and cycloaliphatic polyisocyanates are preferred for use in this invention, although aromatic polyisocyanates may occasionally be used. Aliphatic polyisocyanates are the most preferred because of decreased toxicological considerations.

Examples of suitable di- and polyfunctional isocyanates are found in the following list.

toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene bis(cyclohexyl isocyanate)
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyanate
2,4-dimethyl-phenylene diisocyanate
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenyl methane
2,6-dimethyl-4,4'-diisocyanatodiphenyl
2,4-diisocyanatostilbene
3,3-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate p,p',p"-triphenylmethane triisocyanate
trifunctional trimer (isocyanurate) of isophorone diisocyanate
trifunctional bioret of hexamethylene diisocyanate
trifunctional trimer (isocyanurate) of hexamethylene diisocyanate
polymeric 4,4'-diphenylmethane diisocyanate Capping of the selected triols or higher polyols with polyisocyanates to form the prepolymers used in this invention is effected using stoichiometric amounts of reactants. The isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may be carried out at about 20° to about 150° C., under dry nitrogen, for about 2 hours to about 14 days, preferably in the absence of a catalyst. The preferred temperature is about 125° C. The reaction is terminated when the isocyanate concentration approaches theoretical values. The time period will be a function of the polyol and the polyisocyanate used and the temperature at which the reaction is conducted. Polymerization occurs much more rapidly when aromatic polyisocyanates are used than with aliphatic polyisocyanates. Similarly, the reaction will be more rapid with increased temperatures.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete endcapping eliminates excessively high viscosity in the prepolymer by avoiding undue amounts of chain extension. However, a slight excess of isocyanate, i.e., up to about ten percent can be used.

It is characteristic of the present polymer system that the isocyanate content is very low. This is achieved by employing high molecular weight polyols and by avoiding excessive quantities of isocyanate in the end-capping reaction so that free isocyanate monomers are kept at a minimum. The isocyanate concentration in the prepolymer should be above 0.05 milliequivalents per gram and preferably about 0.1 to about 0.43 milliequivalents per gram, for prepolymers formed from triols or high polyols of about 7000 to 30,000 MW.

In general, the literature describing the polymers used in this invention describes a process which uses a large excess of water (see U.S. Pat. No. 4,137,200 to Wood).

For many applications, this process results in a foam which requires drying after production. The inventors have found that the combined use of an aliphatic diisocyanate-based prepolymer (Prepolymer F as an example), the Prepolymers A-D which act as a surfactant in this system, and the sodium bicarbonate and a non-cytotoxic surfactant can result in a foam with optimal properties using low amounts of water. In this matter the drying time and hence production costs can be reduced. The water (aqueous reactant) can be added in weight ratios of prepolymer:water at least as low as about 20:1. See Examples 10 and 11.

It is also sometimes desirable to add a foaming promoter to the aqueous reactant. Suitable nontoxic promoters include inorganic bases such as sodium bicarbonate or sodium carbonate and are added in amount equaling about 0.5 to 2.0% by weight of the aqueous reactant. It is notable, however, that the organotin and tertiary amine catalysts, while useful in other applications, are generally unnecessary for the practice of the present invention.

The foams of the present invention are suitable as carriers for the metered dosing of medicaments. Such materials can be incorporated in the in various ways.

The foam may be immersed in a solution containing the medicament and allowed to imbibe it. Another method includes adding to medicament in the aqueous component during the foaming step. Thus, when the foam is formed, the medicament is encapsulated within the foam's structural interstices.

Suitable medicaments include, for example, antimicrobial agents such as silver sulfadiazine ("SSD"), and debriding agents such as vibriolysin. The Applicants have found that, if SSD is incorporated into a wound dressing made from the foams disclosed herein, the dressings will tend to inhibit the growth of common bacteria such as *P. aeruginosa* or *S. aureus*.

In the alternative the foam could be lightly chlorinated, for example, by addition of a chlorinating compound such as sodium or calcium hypochlorite to the aqueous component in the foaming step. A Ph adjuster might also be included. In that case, the urethane would react with dilute NaOCl to form N-chloro compounds that would be stable when dry. When wet, they would generate hypochloric acid, which is in equilibrium with chlorine and hydrogen peroxide. The NaOCl aqueous component must be dilute enough to provide a useful level of N-chlorination without weakening the foam. Higher levels of chloride could be incorporated in the foam by encapsulating the chloride in an inert material before mixing with the prepolymer.

The foams of the present invention also possess other advantageous properties. For instance the foams described above show excellent inherent antistatic properties not seen for other polyether polyurethane foams. Embodiments using the foams prepared from the aliphatic polyisocyanate containing prepolymers do not yellow on aging, e.g., in the presence of ultraviolet radiation.

Even further, the foams prepared from hexamethylene diisocyanate (IIHDIII) show substantial resiliency and should be quite useful for protecting and cushioning devices in their packages.

Finally, the foams do not cause corrosion, etching or pitting of certain metals when tested according to methods in MIL-B-81705B, paragraph 4.8.3., Federal Standards 101° C., test method 3005.

The following examples are provided to illustrate the invention and should not be interpreted as limiting the scope thereof or the claims which follow the examples.

EXAMPLE I

Preparation of Prepolymer A

A prepolymer was prepared by mixing 848.8 g of deionized and dried BASF 1123 polyol, a 6800 NW polyether triol comprised of 75% ethylene oxide and 25% propylene oxide. (BASF, Wyandotte Corp, Wyandotte, Mich.) with 91.6 g isophorone diisocyanate (IPDI) in a one liter polyethylene bottle at room temperature with mechanical stirring for 30 minutes. Dry nitrogen was purged over the mix and the bottle was sealed with a screw cap and placed in an electric oven at 85° C. After 11 days the reaction was terminated. The product had an isocyanate value of 0.43 meq/g and a viscosity of 62,000 cps at 25° C. This prepolymer was designated Prepolymer A (low temperature). A prepolymer was prepared in the identical manner except that it was incubated in an electric oven for 2 days at 125° C. This prepolymer was designated Prepolymer A (high temperature).

EXAMPLE II

Preparation of Prepolymer B

A prepolymer was formed by mixing 403.0 g deionized and dried TPEG 20000 ™ (Union Carbide Corp.) with 14.78 g IPDI and 0.21 g Santonox R. TPEG 20000 is a 20,000 MW triol prepared from 100% homopolymeric ethylene oxide. To this mixture 515.0 ml acetonitrile was added to prevent solidification. The resulting mixture was heated as in Example I for 11 days until an isocyanate content of 0.147 meq/g, corrected for solvent (theoretical=0.145 meq/g) was reached. The prepolymer, designated Prepolymer B, was a liquid at room temperature.

EXAMPLE III

Preparation of Prepolymer C

A prepolymer was formed by mixing 1570.0 g deionized and dried BASF 1123 polyol (BASF) with 200.0 g Desmodur W ™ methylene bis(cyclohexyl diisocyanate) (Mobay Chemical Corp.) The mixture was heated to 85° C. under dry nitrogen for a period of 2-3 days until an isocyanate level of 0.47 meq/g was reached. The resulting prepolymer was liquid at room temperature and had a viscosity of 63,000 cps at 25° C. This prepolymer was designated Prepolymer C.

EXAMPLE IV

Preparation of Prepolymer D

A prepolymer was formed by mixing 300.0 g deionized and dried TPEG 100003 (Union Carbide Corp., Danbury, Conn.) with 22.0 g IPDI and 0.16 g Santonox R. TPEG 10000 is a 10,000 MW triol prepared from 100% homopolymeric ethylene oxide. The mixture was heated at 70° C. under dry nitrogen as in Example I, until isocyanate values reached 0.36 meq/g (theoretical=0.28 meq/g). This prepolymer, designated Prepolymer D, formed a solid when cooled to room temperature.

EXAMPLE V

Preparation of Prepolymer E

A mixture of 500 g (0.5 moles) of Carbowax 1000 and 33.5 g (0.25 moles) of trimethylolpropane was degassed by heating for two hours @70° C. and about 2 Torr. To this was added 542 g (2.07 moles, 18% excess) of Desmodur W, i.e. hexamethylene diisocyanate. The temperature was raised to 70° C. and 0.5 g of stannous octoate was added as catalyst. After 35 minutes, the isocyanate content of the reaction product was 2.19 meq/g and the product was poured into a bottle for storage. After a few days at ambient temperature, the isocyanate content and viscosity had stabilized at 2.00 meq/g and 73,000 cp at 25° C.

EXAMPLE VI

Preparation of Prepolymer F

A polyurethane prepolymer was made using previously described methods (U.S. Pat. No. 4,137,200 and copending U.S. Ser. No. 410,775 by mixing 951.8 g of polyethylene glycol of molecular weight 600, 59.5 g of trimethylolpropane, and 646.3 g of hexamethylene diisocyanate. The reaction was allowed to proceed until the isocyanate content was 1.92 meq/g, when an additional 71.8 g of hexamethylene diisocyanate was added to the mixture. The resulting product, Prepolymer F, had an isocyanate content of 2.15 meq/g and a viscosity of 9,000 cps.

EXAMPLE VII

Preparation of Foams 1. 28 g of the above Prepolymer F was mixed with 2 g of A hydrophilic, gel-forming polyurethane prepolymer known as Prepolymer C. (This prepolymer is the reaction product of a random ethylene oxide:propylene oxide triol of molecular weight approximately 7000 and hydrogenated diphenyl methane diisocyanate (HMDI), such that each hydroxyl group is intended to be end capped with an HMDI group.) To this mixture, 10 g of an aqueous 2% sodium bicarbonate solution was added. After rising and curing, a surprisingly fine-celled and water absorbent foam resulted. The foam was found to be finer-celled than a corresponding foam made without the Prepolymer C, and very hydrophilic compared to a typical coarse-celled foam made by mixing HYPO-LO ® 2002 prepolymer with water, with no surfactant present.

2. 28 g of Prepolymer E was mixed with 2 g of Prepolymer A. Then 10 g of aqueous solution composed of 2% PLURONIC F68, a polyoxyethylene-polyoxypropylene block copolymer containing over 75% by weight polyoxyethylene, and 2% sodium bicarbonate was added, and the foam was allowed to rise. The resulting foam (0.065 g/cm$^3$) was fine-celled, and the cells were open. When one end of the strip was immersed in a 1% saline solution, 3.2 cm of vertical wicking was observed in 1.0 minute, and 6.2 cm of wicking was observed after just over 10 minutes. This amount of wicking is substantially higher than observed when the same foam was made without the Prepolymer A, which showed a vertical wicking height of 2.6 cm in 20 minutes. This reduced level of wicking was observed because the cells were too coarse to allow optimal wicking. In subsequent experiments, it was found that by varying the amount of Prepolymer A, the open-closed cell nature of the foam, cell size, and density could be varied.

3. We also found that a foam very similar to the one described above could be produced by reacting a high molecular weight polyol in situ prior to foaming. 750 g of Prepolymer E was mixed with 83.33 g of a trifunctional, water-soluble ethylene oxide:propylene oxide random copolymer polyol of molecular weight approximately 7500 ("WRG 7000", made for W. R. Grace by Union Carbide). After approximately two hours of reaction at 70° C., the isocyanate content of the mixture dropped about 10% to 1.87 meq/g, indicating that the hydroxyl groups of the polyol had reacted with the Prepolymer E isocyanate groups. The viscosity of this product was 93,000 cps at 25° C., which compared to 71,000 cps for the starting Prepolymer E polyol. 30 g of this product was mixed with 10 g of an aqueous solution containing 2% PLURONIC F68 and 2% sodium bicarbonate. The resulting foam was very similar in cell structure (fine, open cells) to the fine-celled foam described immediately above in Example 1.

In a similar example using a different prepolymer system, and using a "one-shot" prepolymer formation reaction, a polymer was prepared using 500 g of poly(ethylene glycol) of molecular weight 1000, 55 g of WRG 7000 polyol, 22.3 g of trimethylolpropane, and 279 g of toluene diisocyanate. The product resulted in fine-to-medium sized cells when foamed using water alone; this result represents finer cells than would be obtained by foaming HYPOLG ® 2000 polymer (no WRG 7000 additive) with water alone. This preparation was repeated three times with various types of toluene diisocyanate from different suppliers, with substantially the same results.

4. 27 g of Prepolymer F (based on polyethylene glycol, trimethylolpropane, and hexamethylene diisocyanate) were mixed with 3 g of Prepolymer A. Then 10 g of an aqueous solution containing 10% PLURONIC F38 surfactant and 0.1 g of sodium bicarbonate were mixed with the prepolymer combination, and the creaming mixture was spread between polyethylene sheets and squeezed between closely-spaced parallel bars to form a rising foam sheet. After several minutes, a fine, open-celled foam resulted. The cells were much finer than those in a corresponding foam made without the Prepolymer A.

5. 24 g of Prepolymer F was mixed with 6 g of Prepolymer A. Then 10 g of 10% PLURONIC F38 containing 0.1 g of sodium bicarbonate were mixed with the prepolymer combination, and the creaming mixture was spread between polyethylene sheets and squeezed between closely-spaced parallel bars to form a rising foam sheet. After several minutes, a very fine, very soft, open-celled foam resulted. The cells were finer and the foam was softer than those in the previously described foam containing less Prepolymer A (Example 4). The foam had a slippery feel to it, although there was no indication that polymer was extracting out of the foam.

6. A foam was made as in the above example, but 40 g of Prepolymer F was first mixed with 10 g of Prepolymer A. To this mixture 16.7 g of an aqueous solution containing 2% PLURONIC F68 and 2% sodium bicarbonate were added and mixed well. The resulting mixture was quickly poured between two polyester sheets and passed between two closely-spaced bars to form a sheet approximately 0.2 inches in thickness. This foam had a density of 0.059 g/cm$^3$ and held 35.27 times its weight in water under no applied pressure. Surprisingly, saline wicked up 4.5 cm in one minute and 9.5 cm in 20 minutes when a strip of the foam was immersed in a pan of saline solution. This wicking compares very favorably to the 0.3 cm in one and twenty minutes when a similar foam strip made by reacting Prepolymer F without Prepolymer A-D was examined in a similar test.

7. A gel-forming analog to the Prepolymer A, but based on toluene diisocyanate, was made by mixing 900 g of the previously mentioned "WRG 7000" polyol with 69 g of toluene diisocyanate. After mixing well, the reaction was performed in a closed jar at 85° C. until the total isocyanate content was 0.43 meq/g. This polymer is commercially available as HYPOLO ® Hydrogel prepolymer sold by W. R. Grace Organic Chemicals Division.

Several foams based on these toluene diisocyanate-containing prepolymers were made using standard methods described in the HYPOL polymer product literature. HYPOL 2002 and Prepolymer B were mixed with various proportions and foamed with either water or an aqueous solution containing 2% PLURONIC F68 in 1:1 prepolymer:aqueous weight ratios. Properties are listed below. In the cell size determination, the predominant cell size is underlined.

| Composition | Cell Size | Time for Drop Wetting | 1 min. Vertical Wicking |
|---|---|---|---|
| 2002 (water) | medium-large | >15 sec | 0.2 cm |
| 2002 (F68) | fine-medium | 1 sec | 1.5 cm |
| 2002:B 98:2 (water) | fine-medium | >15 sec | 0.3 cm |
| 2002:B 98:2 (F68) | fine-medium | 1–2 sec | 2.5 cm |
| 2002:B 95:5 (water) | fine-medium | >15 sec | 0.3 cm |
| 2002:B 95:5 (F68) | fine | 2 sec | 2.4 cm |
| 2002:B 90:10 (water) | fine-medium | >15 sec | 0.4 cm |
| 2002:B 90:10 (F68) | very fine | 5–6 sec | 2.7 cm |

The water-drop absorption/wetting increased with gel-forming prepolymer incorporation, but the wickability also increased. These results were consistent with the visual observation that the foams were becoming less reticulated as the amount of high molecular weight modifier increased in the composition. In this particular system, the use of this modifier, in the absence of the PLURONIC F68 surfactant, led to smaller and finer cells and led to small improvements in wettability. It was also noted that the incorporation of Prepolymer B greatly aided the mixing process; that is, the prepolymer and water components were much more easily combined when the gel-forming prepolymer was present, even in small amounts.

8. The following foams were produced:

a. 30 g of the toluene diisocyanate-based HYPOL 2002 prepolymer were mixed thoroughly and quickly with 15 g of an aqueous solution containing 2% PLURONIC F68 surfactant. The foam was allowed to rise, cure and dry. The resulting foam consisted of coarse, open, reticulated cells.

b. 24 g of HYPOL 2002 prepolymer were mixed with 6 g of the isophorone diisocyanate-based Prepolymer A; then 15 g of an aqueous solution containing 2% PLURONIC F68 surfactant was quickly and thoroughly combined with the prepolymer, and the resulting foam was allowed to rise and dry. This fine-celled foam had a few closed or nearly closed cells.

c. 30 g of the hexamethylene diisocyanate-based Prepolymer F were mixed thoroughly and quickly with 15 g of an aqueous solution containing 2% PLURONIC F68 surfactant and 2% sodium bicarbonate. The foam was allowed to rise, cure and dry. The resulting foam consisted of coarse, open, reticulated cells.

d. 24 g of the hexamethylene diisocyanate-based Prepolymer F were mixed with 6 g of the toluene diisocyanate-based HYPOLO ® HYDROGEL prepolymer, obtained from the Organic Chemicals Division of W. R. Grace & Co.—Conn. (This polymer is very similar to the Prepolymer B previously described.) Then, 15 g of an aqueous solution containing 2% PLURONIC F68 surfactant and 2% sodium bicarbonate was quickly and thoroughly combined with the prepolymer, and the resulting foam was allowed to rise and dry. This fine-celled foam had a few closed or nearly closed cells.

The foams described in a–d above were evaluated for vertical wicking behavior as a test of wettability. Results are shown below:

| Foam | Vertical Wicking (cm) after: | | |
|---|---|---|---|
| | 15 sec | 1.0 min | 20 min |
| a | 0.5 | 1.2 | 1.4 |
| b | 1.9 | 3.2 | 6.2 |
| c | 1.0 | 1.2 | 1.3 |
| d | 1.5 | 3.0 | 3.4 |

The data in the table show that the addition of the gel-forming prepolymer results in foams having improved hydrophilicity and greater water uptake. This example also indicates that the type of isocyanate used in the foam- and gel-forming prepolymers is not a critical factor in the improvement of properties.

9. A total of 40 g of Prepolymer F was mixed with 10 g of Prepolymer A. Then, an aqueous phase consisting of 3 g of a solution containing 10% PLURONIC F68 in deionized water was mixed with 0.2 g of sodium bicarbonate. The prepolymer and aqueous phases were mixed with an electric mixer, and the foam was allowed to rise in the cup. A portion of the prepolymer-aqueous mixture was poured between two pieces of polyethylene, pulled between two closely-spaced horizontal bars, and the resulting thin sheet was allowed to rise between the polyethylene sheets. After about 2.5 minutes at room temperature, the foam was fully cured, was not tacky, and was very similar to the foam of similar composition (but made with more water) described in Example 5. The only significant difference between the high- and low-water-containing foams was in the amount of water used to make them.

10. A number of comparative foams were synthesized with similar "low" amounts of water, as described below:

| Prepolymer | Aqueous Component | Description of Foam |
|---|---|---|
| a. HYPOL FHP-4000 (40 g) | 10% PLURONIC F68 (3 g) | Very tacky foam. Coarse, open cells. |
| b. HYPOL FHP-4000 (40 g) | 10% PLURONIC L62 (3 g) | Very tacky foam. Closed cells; foam "shriveled up". |
| c. HYPOL FHP-4000 (50 g) | 10% PLURONIC F68 (3 g) | Very tacky foam. Closed cells; foam "shriveled up". |
| d. HYPOL FHP-4000 (40 g) | 10% PLURONIC F68 (3 g) | Very tacky foam. Closed cells; foam "shriveled up". |
| e. Prepolymer A (10 g) | | |
| f. HYPOL FHP-2002 (50 g) | 10% PLURONIC F68 (3 g) | Very tacky foam. Mostly closed cells |
| g. HYPOL FHP-2002 (40 g) | 10% PLURONIC F68 (3 g) | Very tacky foam. Closed cells. |
| Prepolymer A (10 g) | | |

In all of these examples, the PLURONIC F68 surfactant was used, because this surfactant is well known to result in the highest degree of cell "openness" and reticulation in HYPOL foams (see HYPOL polymer product literature). Yet, it is observed that with these small amounts of water, even these F68-based materials are very closed-celled. It appears that, as a result of these experiments, that the use of an aliphatic diisocyanate-based Prepolymer F as an example), the Prepolymer A which can act as a surfactant in this system, and the sodium bicarbonate are all necessary for optimal properties using these low amounts of water.

EXAMPLE VIII

Incorporation of Medicament

Sample Preparation

All samples were prepared with a polymer mixture (80%$_w$ Prepolymer F and 20%$_w$ Prepolymer A) and two concentrations of SSD (1.5 and 2% by weight), plus an aqueous phase containing 2% surfactant (Pluronic F-68) and 2% sodium bicarbonate. The foam dressing is formed by combining three parts polymer mixture with one part aqueous phase then extruding this mixture through roller bars between sheets of polyethylene. After a two-minute cure time, the polyethylene is removed and the 2 to 3 Mm thick sheet of foam is suspended to air dry. Dressings are cut onto 13 mm squares having a thickness of 2 to 3 mm. Dressings are placed in sealed bags and stored under refrigeration until needed. Just before testing, they are exposed to UV light for 15 minutes on each side to reduce the possibility of contamination.

Assay Method

This method is based on the ability of SSD to inhibit growth of *PseudoNonas aeruginosa* and *Staphylococcus aureus*. Wound dressing samples are placed on inoculated agar plates, moistened with saline solution, and incubated at 37° C. for 20 hours. Each day, after zones of growth inhibition are measured, the dressings are transferred to freshly inoculated agar plates. This procedure is repeated until the dressing is unable to inhibit bacterial growth.

MEDIA

1) TSB: Tryptic Soy Broth (follow bottle instructions).
2) TSA: Tryptic Soy Agar (follow bottle instructions).
3) TSA/TTC: Tryptic Soy Agar containing 2,3,5-Triphenyltetrazolium chloride (TTC) "Produces red colonies for better visibility."

Preparation: Combine 40 g TSA and 1 g dextrose, Q.X. to 1 liter with water. Autoclave for 15 min. at 121° C. then cool to 70° C. and add 5 ml of a filter sterilized 1% TTC solution. Pour into petri plates.

INOCULUM

1) *Pseudomonas aeruginosa*
2) *Staphylococcus aureus*

Inoculum is prepared fresh daily by transferring cells by loop from 24 hour spread plates to 25 ml TSB in shake flasks and incubating at 37° C./250 RPM, for 2 to 3 hours. The culture broth is serial diluted in sterile PBS > The TSA/TTC plates are inoculated with 100 microliters of the dilution which will produce a cell count between $10^4$ and $10^5$.

METHOD

1) Expose TSA/TTC plates to UV light for 15 minutes.
2) Inoculate plates by spreading 100 microliters of culture suspension over the agar surface to give a $10^4$ cull count.

3) Place dressings aseptically on the surface of the agar then add 200 microliters of sterile phosphate buffered saline (PBS) to each dressing.
4) Seal agar plates with parafilm and incubate at 37° C. for 20 to 24 hours.
5) After incubation, determine the zone of growth inhibition by measuring the total area cleared and then subtracting the area covered by the dressing.
6) The dressings are moistened daily and transferred to freshly inoculated agar plates as in step (3), and the above procedure is repeated daily until the dressings no longer inhibit bacterial growth by the release of antimicrobial.

The 1.5% SSD dressing (TG16124-38-4) was freshly prepared, whereas the 1.0% SSD dressing (JW16417-16-2) was prepared 4 months before the test.

The foam wound dressings alone did not inhibit the growth of either *P. aeruginosa* or *S. aureus*. At an inoculum level of $10^9$ * C.FU, 1.4 and 2.0% SSD dressings produced zones of *P. aeruginosa* growth inhibition around the dressings for 4 and 5 days, respectively (Table 1); however the growth of *S. aureus* was inhibited for only 1 and 2 days, respectively (Table 2). Based on these results, the *S. aureus* inoculum was reduced to $10^4$ * C.FU. However, the 1.5% SSD wound dressing produced a zone of growth inhibition for only one day, the same as the $10^9$ CFU inoculum (Table 3). These results suggest that SSD is not as effective against *S. aureus* as it is against *P. aeruginosa*.

After the zones of growth inhibition were no longer detected around each dressing (1.5 and 2.0% SSD), the study was continued until no inhibition was observed under the dressings. As a result, the area under each dressing did not become completely contaminated with *S. aureus* until 2 to 3 days after zones of inhibition were no longer observed (Tables 1, 2 and 3).

TABLE 1

Growth Inhibition of *P. aeruginosa* ($10^9$ CFU) By SSD Containing Foam Wound Dressings

| DAYS (a) | SSD (%) | AREA OF INHIBITION (mm²) (b) | % INHIBITION UNDER DRESSING |
|---|---|---|---|
| 1. | 1.5 | 102 | 100 |
|  | 2.0 | 121 | 100 |
| 2. | 1.5 | 752 | 100 |
|  | 2.0 | 784 | 100 |
| 3. | 1.5 | 570 | 100 |
|  | 2.0 | 572 | 100 |
| 4. | 1.5 | 178 | 100 |
|  | 2.0 | 200 | 100 |
| 5. | 1.5 | 0 | 0 |
|  | 2.0 | 84 | 100 |
| 6. | 2.0 | 0 | 90 |
| 7. | 2.0 | 0 | 0 |

(a) Incubation at 37° C., transferred and moistened daily.
(b) Total area of inhibition minus area of wound dressing.

TABLE 2

Growth Inhibition of *S. aureus* ($10^9$ CFU) By SSD Containing Foam Wound Dressings

| DAYS (a) | SSD (%) | AREA OF INHIBITION (mm²) (b) | % INHIBITION UNDER DRESSING |
|---|---|---|---|
| 1 | 1.5 | 32 | 100 |
|  | 2.0 | 48 | 100 |
| 2. | 1.5 | 0 | 90 |
|  | 2.0 | 32 | 100 |
| 3. | 1.5 | 0 | 40 |
|  | 2.0 | 0 | 50 |
| 4. | 1.5 | 0 | 0 |

TABLE 2-continued

Growth Inhibition of *S. aureus* ($10^9$ CFU) By SSD Containing Foam Wound Dressings

| DAYS (a) | SSD (%) | AREA OF INHIBITION (mm²) (b) | % INHIBITION UNDER DRESSING |
|---|---|---|---|
|  | 2.0 | 0 | 0 |

(a) Incubation at 37° C., transferred and moistened daily.
(b) Total area of inhibition minus area of wound dressings.

TABLE 3

Growth Inhibition of *S. aureus* ($10^4$ CFU) By SSD Containing Foam Wound Dressings

| DAYS (a) | SSD (%) | AREA OF INHIBITION (mm²) (b) | % INHIBITION UNDER DRESSING |
|---|---|---|---|
| 1. | 1.5 | 159 | 100 |
| 2. | 1.5 | 0 | 95 |
| 3. | 1.5 | 0 | 65 |
| 4. | 1.5 | 0 | 10 |
| 5. | 1.5 | 0 | 0 |

(a) Incubation at 37° C., transferred and moistened daily.
(b) Total area of inhibition minus area of wound dressings.

What is claimed:

1. A hydrophilic foam comprising the reaction product of
   (a) a first polyol having a hydroxyl functionality of at least 2 and a number average molecular weight in the range of 200 to 20,000 and which contains at least 40 mole percent oxyethylene,
   (b) a second polyol having a hydroxyl functionality in the range of about 3 to 8,
   (c) a triol or higher polyol made up of at least 75% oxyethylene monomers, having a molecular weight of about 7000 to about 30,000,
   (d) a polyisocyanate having an average isocyanate functionality in the range of about 2.0 to 2.8, and
   (e) a foaming promoter.

2. The hydrophilic foam of claim 1 wherein (a) contains about 80–100 mole percent oxyethylene.

3. The hydrophilic foam of claim 1 wherein the ratio by weight of the combined polyols (a) and (c) to an aqueous reactant is in the range of about 0.05:1 to 10:1.

4. The hydrophilic foam of claim 1 wherein the ratio by weight of the combined prepolymers (a) and (c) to an aqueous reactant is in the range of about 1:1 to 4:1.

5. The hydrophilic foam of claim 1 wherein (d) is toluene, diisocyanate, hexamethylene diisocyanate, methylene bis(cyclohexyl isocyanate) isophorone diisocyanate, or mixtures thereof.

6. The hydrophilic foam of claim 2 wherein
   (a) and (c) are polyethylene glycol derivatives,
   (b) is trimethylol propane, and
   (d) is toluene diisocyanate, isophorone diisocyanate, hexamethylene diisocyanate, methylene bis(cyclohexyl isocyanate) or mixtures thereof.

7. The hydrophilic foam of claim 1 wherein (e) is sodium carbonate or bicarbonate.

8. The hydrophilic foam of claim 1 further comprising (f) a non-cytotoxic surfactant.

9. The hydrophilic foam of claim 8 wherein (f) is a polyoxyethylene-polyoxypropylene block copolymer containing over 75% by weight polyoxyethylene.

10. A hydrophilic foam comprising the reaction product of a polyurethane prepolymer (I), which is prepared from a reaction mixture comprising:

(a) first polyol having a hydroxyl functionality of at least 2 and a number average molecular weight in the range of 200 to 20,000 and which contains at least 40 mole percent oxyethylene,
(b) a second polyol having a hydroxyl functionality in the range of about 3 to 8 and
(c) a polyisocyanate having an average isocyanate functionality in the range of about 2.0 to 2.8, with a biocompatible prepolymer (II), which is a triol or higher polyol made up of at least 75% oxyethylene monomers, said polyol having a molecular weight of about 7000 to about 30,000, said polyol having essentially all of the hydroxyl groups capped with aliphatic or cycloaliphatic polyisocyanates.

11. The hydrophilic foam of claim 10 wherein (a) contains about 80-100 mole percent oxyethylene.

12. The hydrophilic foam of claim 10 wherein the ratio by weight of the combined prepolymers I and II to an aqueous reactant is in the range of about 0.1:1 to 10:1.

13. The hydrophilic foam of claim 10 wherein the ratio by weight of the combined prepolymers I and II to the aqueous reactant is in the range of about 1:1 to 4:1.

14. The hydrophilic foam of claim 10 wherein the ratio by weight of the combined prepolymers I and II to the aqueous reactant is in the range of about 4:1 to 20:1.

15. The hydrophilic foam of claim 10 wherein
(a) is polyethylene glycol
(b) is trimethylol propane, and
(c) is toluene diisocyanate, isophorone diisocyanate, hexamethylene diisocyanate, or mixtures thereof.

16. The hydrophilic foam of claim 10 wherein the hydroxyl groups of prepolymer II are capped with isophorone diisocyanate or hexamethylene diisocyanate.

17. The hydrophilic foam of claim 10 further comprising (d) a foaming promoter.

18. The hydrophilic foam of claim 17 wherein (d) is sodium carbonate or bicarbonate.

19. The hydrophilic foam of claim 10 further comprising (e) a non-cytotoxic surfactant.

20. The hydrophilic foam of claim 19 wherein (e) is a polyoxyethylene-polyoxy propylene block copolymer containing over 75% by weight polyoxyethylene.

21. The hydrophilic foam of any of claims 1-6 and 7-9 in combination with a medicament.

22. The hydrophilic foam of claim 21 wherein the medicament is silver sulfadiazine, a zinc salt or vibriolysin.

23. The hydrophilic foam of any of claims 1-6 and 7-9 further comprising a chlorinating compound.

24. The hydrophilic foam of claim 23 wherein the chlorinating compound is sodium hypochlorite or calcium hypochlorite.

* * * * *